(12) United States Patent
Skocic

(10) Patent No.: US 10,296,716 B1
(45) Date of Patent: May 21, 2019

(54) SYSTEM OF AND METHOD FOR COLLECTING AND TRANSMITTING ADVANCE CARE PLANNING AND DIRECTIVES DOCUMENTATION

(71) Applicant: MLP Technology, Inc., Hiram, OH (US)

(72) Inventor: Ruth E. Skocic, Hiram, OH (US)

(*) Notice: Subject to any disclaimer, the term of this patent is extended or adjusted under 35 U.S.C. 154(b) by 323 days.

(21) Appl. No.: 15/364,028

(22) Filed: Nov. 29, 2016

Related U.S. Application Data

(63) Continuation-in-part of application No. 14/877,967, filed on Oct. 8, 2015, and a continuation-in-part of application No. 13/531,888, filed on Jun. 25, 2012, and a continuation-in-part of application No. 13/492,537, filed on Jun. 8, 2012, now abandoned, and a continuation-in-part of application No. 12/204,560, filed on Sep. 4, 2008, now Pat. No. 8,234,125, and a continuation-in-part of application No. 11/962,267, filed on Dec. 21, 2007, now abandoned, and a continuation-in-part of application No. 11/592,913, filed on Nov. 6, 2006, now abandoned.

(51) Int. Cl.
| | | |
|---|---|---|
| G06F 16/00 | (2019.01) | |
| G06F 19/00 | (2018.01) | |
| G06F 21/62 | (2013.01) | |
| H04L 29/06 | (2006.01) | |
| G16H 10/60 | (2018.01) | |
| G06F 16/13 | (2019.01) | |

(52) U.S. Cl.
CPC ............ *G06F 19/328* (2013.01); *G06F 16/13* (2019.01); *G06F 21/6245* (2013.01); *G16H 10/60* (2018.01); *H04L 63/08* (2013.01)

(58) Field of Classification Search
None
See application file for complete search history.

(56) References Cited

U.S. PATENT DOCUMENTS

| | | |
|---|---|---|
| 5,193,855 A | 3/1993 | Shamos |
| 5,241,466 A | 8/1993 | Perry |
| 5,291,399 A | 3/1994 | Chaco |
| 5,325,294 A | 6/1994 | Keene |
| 5,499,293 A | 3/1996 | Behram et al. |
| 5,651,067 A | 7/1997 | Ahrens et al. |
| 5,651,117 A | 7/1997 | Arbuckle |
| 5,659,741 A | 8/1997 | Eberhardt |
| 5,664,109 A | 9/1997 | Johnson et al. |
| 6,031,910 A | 2/2000 | Deindl et al. |
| 6,034,605 A | 3/2000 | March |
| 6,126,204 A | 10/2000 | Arkinstall |
| 6,845,448 B1 | 1/2005 | Chaganti et al. |

(Continued)

OTHER PUBLICATIONS https://www.cms.gov/Medicare/Medicare-Fee-for-Service-Payment/PhysicianFeeSched/Downloads/FAQ-Advance-Care-Planning.pdf, 2016, all pages.

*Primary Examiner* — Son T Hoang
(74) *Attorney, Agent, or Firm* — John D. Gugliotta

(57) ABSTRACT

Advanced Care Planning and life planning data management system is provided that work in conjunction with biometric identify validation to compare an individual's biometric data with data on file at a central repository until a match is found, upon which that person's advanced care plan and life planning data is forwarded to and displayed at the station for the provider's contemporaneous utilization.

15 Claims, 4 Drawing Sheets

(56) References Cited

U.S. PATENT DOCUMENTS

| | | | |
|---|---|---|---|
| 6,845,488 B1 | 1/2005 | Shim et al. | |
| 7,039,628 B2 | 5/2006 | Logan, Jr. | |
| 7,102,516 B2 | 9/2006 | Orman | |
| 7,328,276 B2 | 2/2008 | Alisuag | |
| 7,542,912 B1 * | 6/2009 | Durand | G06F 19/322 |
| | | | 705/2 |
| 7,668,734 B2 | 2/2010 | Pugh | |
| 8,147,419 B2 | 4/2012 | Krauss | |
| 8,234,125 B2 | 7/2012 | Skocic | |
| 2001/0044732 A1 | 11/2001 | Maus | |
| 2002/0188473 A1 | 12/2002 | Jackson | |
| 2003/0120515 A1 | 6/2003 | Geller | |
| 2003/0233254 A1 | 12/2003 | Hamilton | |
| 2006/0064319 A1 * | 3/2006 | Loevner | G06F 19/3418 |
| | | | 705/2 |
| 2006/0271543 A1 * | 11/2006 | Dodson | G06F 17/30011 |

\* cited by examiner

US 10,296,716 B1

SYSTEM OF AND METHOD FOR COLLECTING AND TRANSMITTING ADVANCE CARE PLANNING AND DIRECTIVES DOCUMENTATION

RELATED INVENTIONS

The present invention is a Continuation in Part of U.S. Serial No. U.S. Ser. No. 11/962,267, filed on Dec. 21, 2007, and a Continuation in Part of U.S. Ser. No. 13/531,888 filed on Jun. 25, 2012 and a Continuation in Part of U.S. Ser. No. 12/204,560 filed on Sep. 4, 2008, all of which claims the benefit of 60/876,048.

The present invention is also a Continuation in Part of co-pending U.S. Ser. No. 14/877,967 filed on Oct. 8, 2015 which was a continuation of Ser. No. 11/592,913 filed on Nov. 6, 2006.

BACKGROUND OF THE INVENTION

1. Field of the Invention

The present invention relates generally to an all-inclusive method of collecting all the documentation related to the advanced care planning ad advance directives of future patients and, more specifically, to a system for and method that prepares an advance care planning and advanced directives declaration documentation and stores an authenticated copy of the information related to end of life planning, wills, medical team planning, family planning funeral planning estate planning and the like as part of a user's electronic medical records or comparable network-enabled system for purposes of making the information obtainable to authorized providers.

2. Description of the Related Art

The present invention relates to a new method of and system for implementation of Advanced Care Planning (ACP) services including, inter alia, legal advance healthcare directives, in a manner that stores participating client's information, inclusive to all areas of future care, such as to allow all stakeholders or care providers in need of such information to securely, quickly and confidentially access needed ACP information in a patient-specific manner, including end of life planning, wills, medical team planning, family planning, funeral planning, estate planning and the like.

There are a number of systems in place whereby patients can store personal information at a single location and selectively authorize it to be distributed to various entities via a communication network. Most recently electronic medical records (EMR) and electronic health records (EHR) have been implemented widely through the health care delivery infrastructure. An EMR contains the standard medical and clinical data gathered in one provider's office. An EHR goes beyond the data collected in the provider's office and include a more comprehensive patient history. Unlike EMRs, EHRs also allow a patient's health record to move with them—to other health care providers, specialists, hospitals, nursing homes, and even across states.

An EMR is more beneficial than paper records because it allows providers to track data over time, identify patients who are due for preventive visits and screenings, monitor how patients measure up to certain parameters, such as vaccinations and blood pressure readings, and improve overall quality of care in a practice.

The information stored in EMRs is not easily shared with providers outside of a practice. A patient's record might even have to be printed out and delivered by mail to specialists and other members of the care team.

A search of the prior art did not disclose any patents that read directly on the claims of the instant invention; however, the following references were considered related.

U.S. Pat. No. 6,845,488, issued Jan. 18, 2005, teaches a method for automatically disbursing a user's personal information to authorized requesters using a server computer coupled to a database. According to this patent, users self-enter personal information over the internet or an extranet or similar network and authorize the entities online it can be transmitted to. The problem with this method is that the information a user provides is not reliable, thus its use in health care is limited.

The crux of the present method is that one step requires the comprehensive collection of all forms relating to advance directives, including legal documents, the validity and authenticity of which must be certified before the information is stored on the main frame and forwarded to providers.

It is the object of many systems to provide a web-based, network based medical records storage and retrieval system. Of considerable relevance is U.S. Pat. No. 7,039,628, published on May 2, 2006, according to which medical records are maintained on a common server that permits treating physicians to enter and access the information at remote sites over the Internet™. The system provides medical care providers with a complete record of all patient's prior treatment, surgical procedures, immunizations, allergies, blood type and other important data. Review of the records alleviates the number of adverse patient problems arising from medical record unavailability and mismanagement, such as mis-diagnosis and the prescription of contra-indicated drugs. The present system is however distinguishable from the former because the record maintained pertain to the client's wishes for future medical care and not to the client's records relating to past care. Another distinction is that clients' wishes will supersede physicians' discretion because some of the documents maintained in the present system will be legal ones, the directives of which will have to be given complete weight.

The urgent need for immediate access to information in emergencies is recognized in U.S. Pat. No. 5,241,466, issued Aug. 31, 1993. This invention provides a central repository for important documents, such as living wills, durable powers of attorney, authorizations for organ donations and insurance information. The depository will process requests, retrieve the associated information and transmit it to authorized requesters. According to this system, the customer sends to the depository a completed application form including personal information and necessary documents. The application is checked for validity and completeness and then its stored in a secure archive operated by the repository. The information requested by authorized entities is retrieved and transmitted upon request to them via facsimile, telephone, postal service or electronic mail.

With widespread EMR and EHR adoption and the ability for a patient to own and beneficially use his or her medical care history, a need now exists to create the next area of data identification, coordination and usage to improve the delivery of future health care, namely, advance healthcare directives and advanced care planning. With increased longevity of our population, age related long term care planning becomes not just a matter for every individually, but ultimately requires information, direction, and decisions to be made in conjunction with a wider group of stakeholders. These include family, healthcare providers, as well as long term assisted living and care facilities. Additionally, the need for an advanced healthcare directives, medical directive or advance decision, have long been felt. Such needs are conventionally implemented in the form of legal documents (created between attorney and client) in which a person specifies what actions should be taken for their health if they are no longer able to make decisions for themselves because of illness or incapacity.

Further, while discussions of many legal issues (e.g. living will, health care proxy, heath care durable power of attorney, and medical orders for life sustaining treatment) have traditionally been performed in counsel between patients and their attorneys, these needs cross over broadly with discussion of advanced care planning between patients and their medical care providers.

Such needs have recently been codified as a medical necessity available for payment reimbursement under Medicare, namely:

"CPT Code 99497—Advance care planning including the explanation and discussion of advance directives such as standard forms (with completion of such forms, when performed), by the physician or other qualified health care professional; first 30 minutes, face-to-face with the patient, family member(s), and/or surrogate."

And

"CPT Code 99498—each additional 30 minutes (List separately in addition to code for primary procedure)"

Since such services have not existed until revised rules were promulgated on Jan. 1, 2016, no method of implementing such Advanced Care Planing nor system for providing the necessary consultation and implementation of Advance Directives documentation have yet existed. Current coordination between patient/client, and elder law attorney, and senior care physicians is not currently efficient in time, costs, and result. Such inherent inefficiencies will be compounded by the burgeoning senior citizen population which, according to the latest U.S. Census Bureau document, shown that the nation's population aged 65 and older comprise more that 40 million people.

In addition, EMR systems at hospitals, physician networks, coding, or billing entities do not have a direct basis to share information from the patent to the physician, hospital or other caregiver from one network to another outside of a specific caregiver EMR or EHR network server unless they share the same practice management system and IT technology (such as McKesson, Allscripts or the like). Organizations or states are trying to create centralized data systems which do store advanced directives and share across EMR systems; however, due to the nature of hospital network competition and networks pushing back on what data and what information they will share and other hospitals not wanting to participate in the integrational system of sharing patient data; our system, data, and technology allows for a stand alone process between all networks and stake holders; an integration to stakeholders systems currently used or a managed technology system that allows to plug and play with all stakeholders for the betterment of each patient and for their data.

Furthermore in the present inventions a complex of educational elements are used to educate the patient and all caregiver stakeholders in what ACP and life planning is and how important collaborative efforts are and what the present invention does to meet collaborative efforts. Stakeholders and other network systems are not built to meet specific requirements of HIE (health information exchange) and lack the patient experience and collaboration in their business methods and systems because although they offer care to patients their systems are built from their business model and not specific to the care of a single individual.

Consequently, a need exists for a means of effectively and efficiently routinize the implementation of advance care planning and advance directive creation as well as subsequent access to such products throughout the current legal and medical delivery infrastructure. Such a need exists now, more than ever, for a comprehensive method of collecting all the documentation related to the advance directives of clients and, more specifically, to a method that stores copies of the authenticated documents on a computer main frame for purposes of making them speedily accessible by web link to hospitals, insurance companies, donor registries, courts and any other authorized providers.

In addition to the hospital and physician networks ACP is reimbursed payment through Medicare and in the future more insurance and reimbursements of care payments will also follow suit of Medicare (CMS). This present system also allows for such agencies who reimburse to have the criteria of analytic analysis, tracking, data collection, time spent per patient on care planning and life planning, and other areas where data collection is relevant to the needs of ACP and ACP reimbursements.

The present invention addresses these current needs and is further adaptable to suit such future needs.

SUMMARY OF THE INVENTION

It is therefore an object of the present invention to provide for an improved method of collecting, storing and accessing client's advance care planning and healthcare directives.

It is a feature of this invention to assist people in creating a system for and method of implementing advance care planning and collecting, retaining and using such plans or directives in a manner that provide efficiency of use and operation for all stakeholders in medical or end of life care or decision making.

It is a further feature of the present invention to provide these and other objects and features in a manner that comply with the requirements under federal rules of the Centers for Medicare and Medicaid Services (CMS)[1] for payment of advance care planning services under the physicians fee schedule.

[1] 80 Fed. Reg. 70956

Briefly described according to the present invention, a method of and system for the collection, storage, assess, usage, and insurance reimbursement for advanced care planning services and advanced health directives is provided. One step in the present method provides for the secure verification of identity of a patient or user for correlation with his or her unique advanced care plan and/or advance health directives. In a preferred aspect of the present invention the use of biometric data is used as a user's identifier. Biometric data may include fingerprints, minutia prints, pulse, DNA, etc. or any similar or equivalent unique distinctive, measurable characteristics used to label and describe individuals. In another preferred aspect of the present invention a functional unique identifier for authentication, such as a smart card, personal identification number, multi-factor authentication, or other electronic or systemic equivalent thereof may be use and should be considered within a broad range of equivalents within the overall authentication step. A mobile device may be provided that is further capable of either capturing the biometric data, or otherwise validating such data through some of or all of iris scanning, 3-D facial imaging or other imaging, wherein impressions of any form (such as, for example, finger, face, eye, etc.) are transmitted to, or their authentication or identification is transmitted to, a separate or remote location in a manner that is fully ISO, SSL and HIPPA compliant. The mobile device may be dedicated or an adapted general purpose or alternate purpose device. The verification of the person's identity and, if desired predetermined information may thereby be provide to the remote user in real time.

In accordance with another aspect of the present invention, a remote authentication mechanism such as, for example, a mobile biometric capture device may be used along with other handheld technology devices, such as a laptop, pocket PCs, smart phone or similar electronic first responder device, in order to operate with captured biometric information. The biometric capture device incorporate technologies that may include iris scanning, DNA reading, smart card reading and 3-D facial imaging (electrical impressions), photo reading, bitmap reading, pulse reading, minutia point reading, transmitted via a private or a public web base wireless laser reading, blood analyzing, etc. A result of these readings is communication network or its equivalent to either a provider at another location remote to the user.

It accordance with another aspect of the present invention, a person's fingerprints, blood matches, 3-D imaging results, iris scan results, smart card results, etc. may be compare to a known reference, either through communication with remote data or at the mobile biometric capture device. The information is use to identify the person whose biometric imprints are viewed and can be used to guide a professional or professionals in making medical, emergency, military and care based decisions for the person. Identification may be done either at the point of care or at the point of decision.

Since the present invention provides for means to authenticate and verify patient identity, and any number of such methods may be utilized, there may not be one simple system for the housing and distribution of all forms at once. For example, a person is admitted to the hospital and subsequently suffers a severe condition that requires resuscitation, but unsuccessful attempts to resuscitate causes him or her to be brain dead. He or she could remain on a ventilator until the next of kin battles the difficult decision as to whether or not the hospital should sustain life support. The costs to the insurance company, the hospital and any effected person waiting on a donor match depend on the time wasted determining this. In the present system, the hospital can access client's resuscitation wishes immediately or pull life support immediately. If the client has any specific organ or bone marrow requests, they can be honored and the organs will also be immediately removed and transported upon a match. Any directives regarding burial preparation or cremation can be immediately accessed as well. Additionally, if the loss of cognitive ability isn't severe and is only temporary, but still requires a power of attorney, the hospital can save crucial care time and money by accessing contacts' information over the network verses locating it.

Another step in the present method provides for guidance in the completion of all documents in the form of counseling patients/clients through their choices, educating patients/clients by hosting seminars, or referring patients/clients to affiliated third party providers for the capture, storage, reporting, and use of such completed plans or forms or billing of such services.

Yet another step in the present invention provide for the information in the patented system and invention to be held at a repository and sent out via various methods of request. The information in the present invention is maintained on a common network of which authorized providers can enter and access at any time. Upon authentication by or for a patient/client the provider may obtain access for immediate use of client's directives, medical records, estate records, etc.

In the providing of necessary information the present invention provides for the preparation of an Advance Directive Declaration Packet that may include an early intervention plan of action for the medical dilemmas in which one may be facing choices about care, such as emergency, operation, terminal illness, temporary or permanent loss of cognitive ability. Included in the packet may be detailed information about a client's medical and procedural wishes in the event there is little hope for full recovery, death is imminent, or life is only possible using artificial means. Since advance care planning and advance health directives are about life choices, and especially end of life choices, the Advance Directive Declaration Packet may include any or all of the following information in one forum: healthcare powers of attorney, Do Not Resuscitate ("DNR") and Do Not Resuscitate Comfort Care ("DNRCC") orders, organ and tissue donation wishes, disclosures, wills, blood type, medical history, medical allergies, known prescription drug use, family medical history, client's known address, the addresses of contacts for emergency, copy of the Health Information Privacy Protection Act ('HIPPA"), and any other information the client may wish to make available. The packet may be all-inclusive and should be completed in its entirety in order for the directives to be dispersed to hospitals, insurance companies, attorneys, executors, courts, and any and all other organizations in need of such information. Also included in the packet is the client's authentication information, such as a biometric identifier (i.e. fingerprints, etc.) for identification and authentication comparison purposes. A common seal, company seal or equivalent may verify the legality of the Advance Directives in those common law jurisdictions that utilizes such legal significance.

It is a unique feature of the present invention to provide for a simple means of effectively educating clients about choices and collecting all of the foregoing information at one time, and in a manner that authenticates not only the information but also the method by which it was collected. The later may be of particular significance for medical reimbursement billing purposes.

A method of collecting client's declarations or directives used in the present invention may include many mechanisms, from individual, in-office consultation, to the hosting of seminars for participating clients over the age of 18 for providing education about their choices and counsel clients through the completion of their respective packets. The completion of the packet, taking of the photo ID, capturing of biometric information of clients and notarization of any legal documents must be completed at the seminar or at a nearby satellite office. Attorneys and notaries may be used on-site to legalize any documents. In any case, the use of educated representatives may be provided to explain the packet and the contents in their entirety upon which clients sign and to insure that they understand the packet and what the early intervention program does. The client may further sign a HIPPA acknowledgment document and a disclosure contract which allows the information to be housed and transported via a web link or any other means of reception. The entire Advance Care Plane and/or Directives may be completed in a single event, or may be accomplished through a series of multiple invents.

In yet another step of the present invention, a separate computer augmented or implemented system is designed to store and mimic completed Advance Directives Declaration Packets and to store all the completed documents as one document in full. The information is stored in one or more electronic databases through a data processing system that utilizes computers through an extranet and data entry personnel. Battery operated portable computer databases may be used at remote locations to house and store each individuals Advance Directives Declaration Packet, authentication data, and verification data.

According to an alternate aspect of the present invention, a portable electronic or data storage device (smart phone, smart card or the like) can be issued to or implemented by each client to carry on their person. If circumstances present a need for information, the local hospital or provider can access information on the card on a machine they possess that is connected to a computer with web access. A secure web link, accessible only to registered users or those under discretion, may interpret and transmit the information such as to allow for the viewing or download of the client's information in part or in full.

In still another step of the present invention, a hospital or care provider may print the Advance Care Plan or Directive in part or in its entirety and follow the client's early choice of procedures. If no electric data storage device is available for accessing, the care provider may go to a web link and input the client's ID Number and scan the client's fingerprint or otherwise authenticate the client's identity. If there is a match, the information becomes accessible or downloadable and its contents accessible to physicians or providers on duty. The web link is specifically designed so that providers can only gain access to a single client's information for each unique user authentication.

In an alternate embodiment of the present invention a computer chip or small disk like device may be issued for storage in a wallet or attachment to or integration with an identity card (i.e. driver's license, etc.). Such a portable chip may be accessible by the system. In yet other alternatives, such solid state data storage such as the electronic chip may be integrated with a piece of jewelry or integrated with a portable communication device.

In an alternate step of the present invention, an adapted embodiment of the present invention may provide a classified web link strictly for governmental use. It is envisioned that employees of the government, military, recipients of Medicare and Medicaid, immigrants, etc. may complete an advance declarations packet at the government's expense. When implemented by immigrants such documentation may be acquired upon entry to the United States or in any satellite where they fill out Green Cards. In such an embodiment, when providers care for immigrants they will immediately have access to the immigrant's legal status in the United States. When implemented by military personnel, access to the present system can be incorporated within their identification tags (i.e. "dog tags"). The information is speedily accessible in the event of a crisis in any theater of operation.

BRIEF DESCRIPTION OF THE DRAWINGS

The advantages and the features of the present invention will become better understood with reference to the following more detailed description and claims taken in conjunction with the accompanying drawings, in which like elements are identified with like symbols, and in which:

DESCRIPTION OF THE PREFERRED EMBODIMENTS

For purposes of the present invention, the term "biometric authentication" is to be broadly construed to include the sensing of minutia points, pulse rates, bone structures, DNA, iris scans, facial images, finger prints, card scans, etc., and sends the readings through a private or a public web server to an end user or provider at a stationary or a mobile computer.

Further, for purposes of the present invention the term "advance care plan" or "advanced directive" should be broadly construed to include any or all such information for implementing the broad objects of the invention whether used by hospitals, long term care facilities, nursing homes, rehabilitation centers, substance abuse treatment facilities, insurance companies, donor registries, and all the other parties having an interest in a user's health care or end of life care. The following exemplary of the information that may be displayed to providers: any medical forms; contact information; probate information: advanced directives information relating to the person's own wishes for care; contact information; medical history; end of life planning; wills or will substitutes; medical team planning; family planning; funeral planning; estate planning and the like as part of a user's electronic medical records or comparable network-enabled system for purposes of making the information obtainable to authorized providers.

The best mode for carrying out the invention is presented in terms of its preferred embodiment, herein depicted within the Figures for purposes of illustrating embodiments of the invention only and not for purposes of limiting the same.

1. Detailed Description of the Figures

Figure 1:
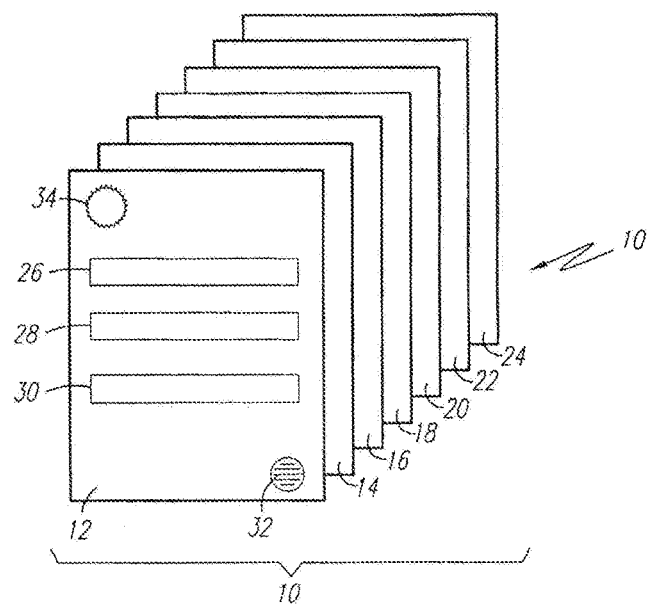
FIG. 1 is a pictural schematic representation of an advance directives documentation for use with the preferred embodiment of the present invention.
Figure 2:
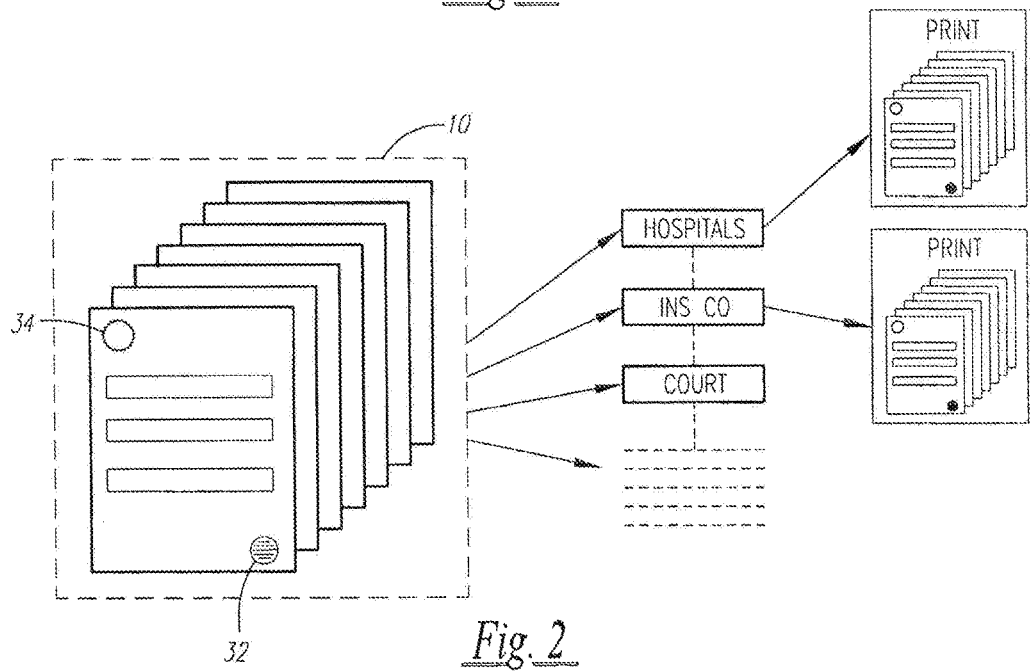
FIG. 2 is a flow diagram showing the delivery thereof for use with the present invention.

As shown in reference to FIG. 1, the present invention provides for the preparation of an Advance Care Plan and Directive Declaration, generally noted as 10. The plan 10 may include a full, thorough and inclusive assembly of information and documents that includes an early intervention plan of action or end of life plan of action 12 for the medical dilemmas in which one may be facing choices about care, such as emergency, operation, terminal illness, temporary or permanent loss of cognitive ability, etc. Included in the packet is detailed information about a client's medical and procedural wishes 14 in the event there is little hope for full recovery, death is imminent, or life is only possible using artificial means. The plan 10 represent's a user's individualized life, health care and end-of-life care choices. The plan 10 may include any or all of the following information in one forum: healthcare powers of attorney 16, DNR or DNRCC orders 18, organ and tissue donation wishes 20, disclosures 22, wills 24, blood type 26, medical history 28, including medical allergies, known prescription drug use, family medical history, client's known address, the addresses of contacts for emergency, copy of HIPPA laws 30 and any other information the client would like to share. The plan 10 is intended to allow for all-inclusive order for the directives to be dispersed to care givers, hospitals, insurance companies, attorneys, executors, courts and any and all other institution or organizations in need of access to such information as shown in conjunction with FIG. 2.

Additionally included in the plan 10 may be a client's photo ID (not shown) and client's fingerprints 32 or other biometric or authentication data for identification purposes. A notarization or common-law seal 34 verifies the legality of any of the Advance Directive legal documents within the plan 10.

Figure 3:
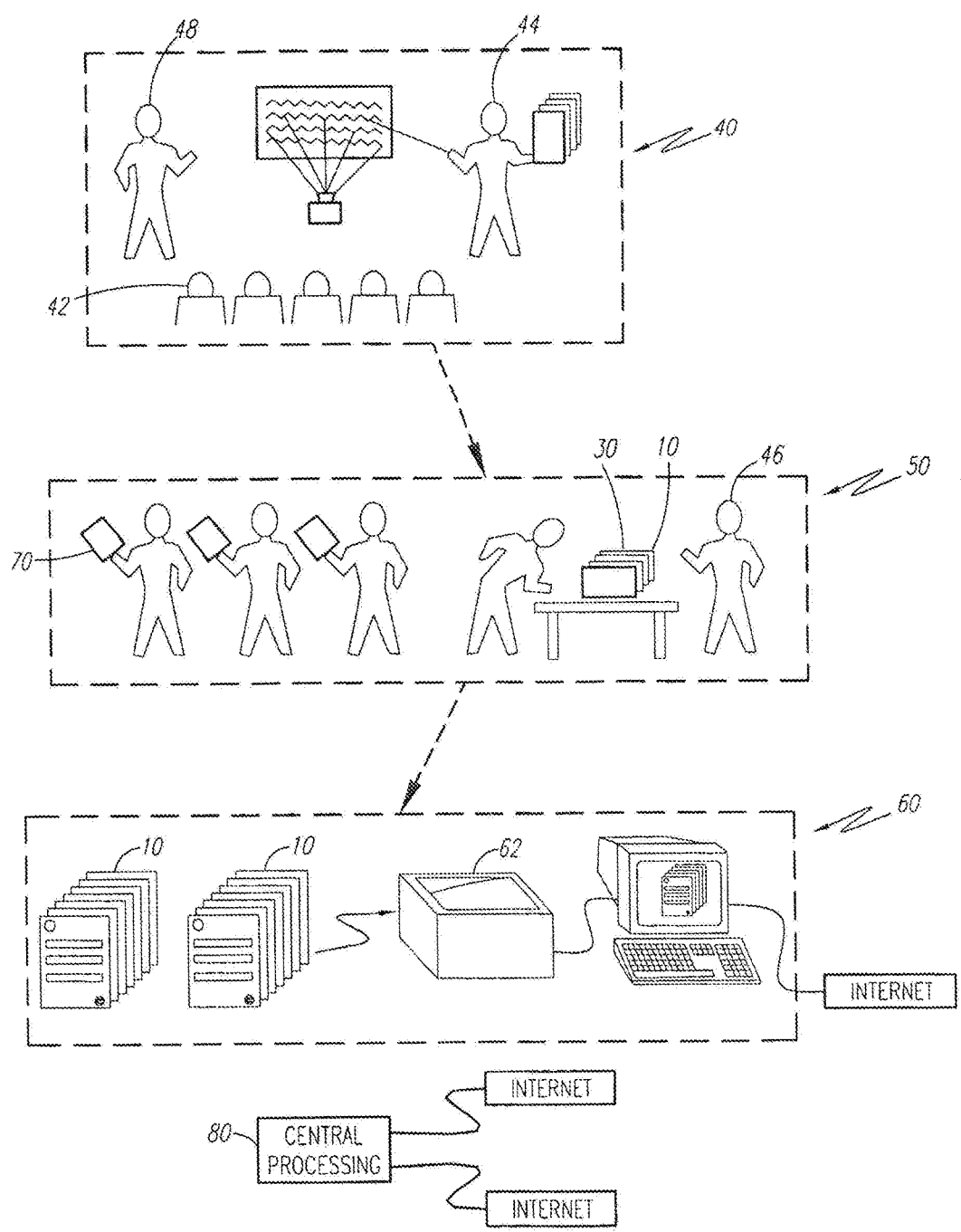
FIG. 3 is a graphical diagram showing a method of collecting and transmitting advance directives documentation according to the present invention.

As shown in conjunction with FIG. 3, it is a unique feature of the present invention to provide for a simple means of effectively educating client's about choices and collecting any or all of the foregoing information at one time or during multiple occasions. The method of collecting client's declarations used in this invention may include through in-office consultation or hosted seminars, generally noted as 40 for participating clients 42 over the age of majority or codified legal age within an appropriate jurisdiction. Any consultation or seminar is intended for the education of clients 42 about their choices and the counseling of clients concerning the completion of their respective plan 10. The completion of the packet 10, fingerprinting or acquisition of a client's biometric data, taking of photo ID and notarization of any documents must be completed at the seminar 50 or at a nearby satellite office (not shown) or at the conclusion of a consultation.

Attorneys 44 and notaries 46 may further be on-site to legalize any documents. Educated representatives 44, 48 explain the packet 10 and the contents in their entirety upon which clients 42 sign that they understand the packet and what the early intervention program does. The client also signs a HIPPA sheet 30 and a disclosure contract which allows the information to be housed and transported via a web link or any other means of reception. The entire Advance Directives Plan 10 can be completed in one days time and a corporate seal placed on its front to identity its legality.

In the present invention, a separate computer program is designed to store and mimic the completed Advance Directive Declaration Packet and to store all the completed documents as one document in full. The information 10 is stored 60 by scanning 62 individual client packets 10, each as individual data files that are encrypted and uniquely identified, using either an otherwise conventional scanner, or, preferably, a unique, portable, battery operated data entry device such as a PDA or other similarly functional device capable of receiving, storing, and transmitting the necessary data files. Such battery operated computer databases used at seminars will have the computer software to house and store each client's Advance Directives Declaration Packet, fingerprints, photo ID and corporate seal. The Packet will then be downloaded to a health care data management system of a type disclosed by or anticipated in U.S. Pat. No. 8,234,125, incorporated by reference as if fully rewritten herein.

Figure 4:
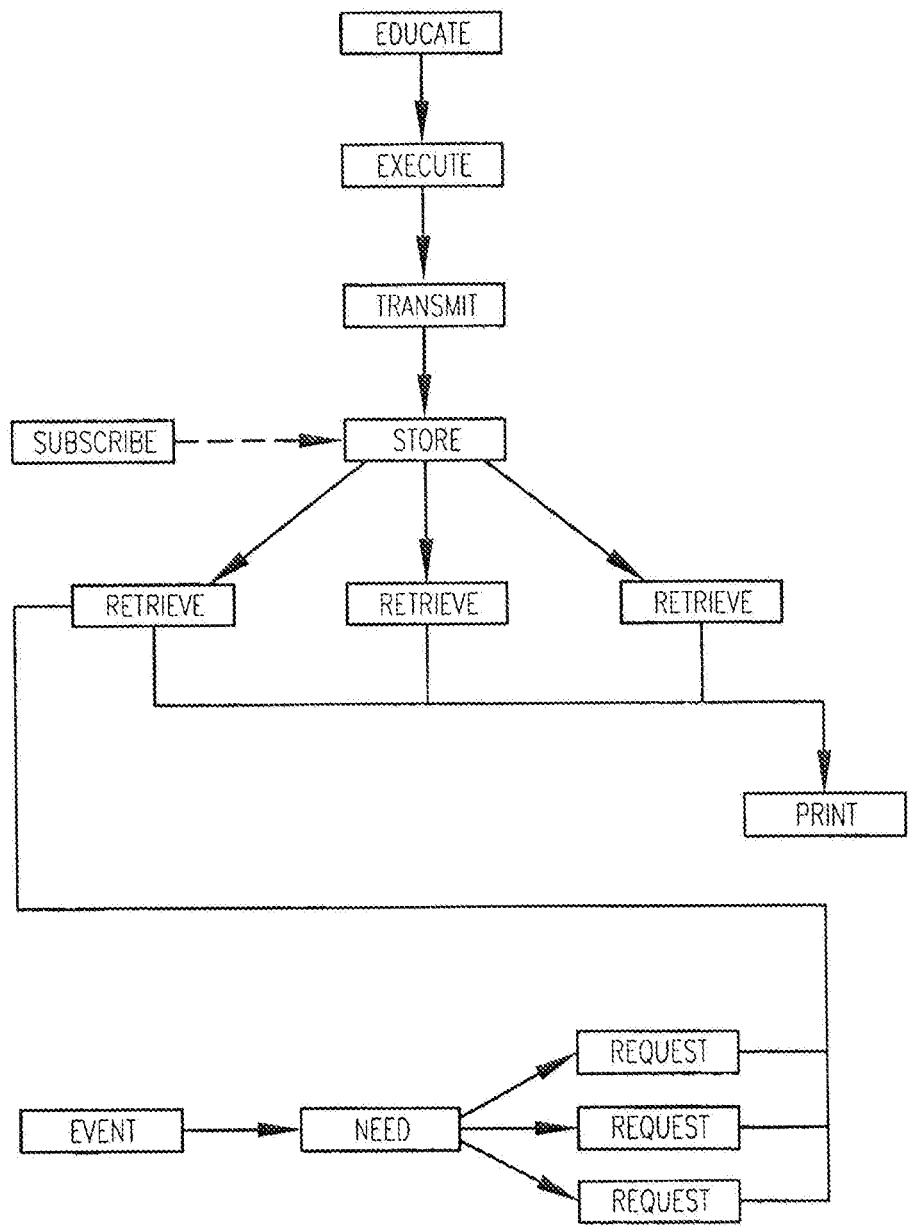
FIG. 4 is a flow diagram outlining the method of the present invention.

As shown best in conjunction with FIG. 3 and FIG. 4, according to one embodiment of the present invention a card 70, similar to a credit card, may be issued to each client to carry. If circumstances present a need for information, the local hospital or provider can either swipe the card on a machine they possess or scan the bar code on the card with a laser connected to a computer providing web access. The data is then transmitted through the internet or through an extranet or similar network to a central processing center 80, where mainframes or server banks are provided to provide centralized security, storage, retrieval, backup, and the like. From this central processing center 80, individual users of the data can access the necessary information available in the packet 10 through subscription, pay per click, or other secure access via the remote network. This secure web link, accessible only to registered users or those under discretion, reads the card and allows for the download of the client's information in full. Then the hospital or provider can print the plan 10 in part or in its entirety and follow the client's early choice of procedures. If no card is available for swiping, the provider may go to the web link and input the client's ID number and scan the client's fingerprint. If there is a match, the packet will be downloaded and its content accessible to physicians and providers on duty.

Such a network link is specifically designed so that providers can only gain access to one client's information at a time based upon a unique authentication (ID Number, fingerprint, photo, name, etc.). All biometric data such as fingerprints may be scanned for personal identification authenticity. Another embodiment of the present invention includes a computer chip or small disk like figure kept in wallets or attached to licenses. The chip can be inputted into a main computer. In the alternative, clients can either store the chip in easily identified jewelry or store a downloadable image of a fingerprint.

It is the object of this invention to also educate the public on the entirety of the Advance Directives Declaration Program. Hospitals, insurance companies, donor registries, and all the other parties mentioned in one client's packet will be notified. Education packages will also be provided to any organization that fits within the profile of an advance declaration directives packet.

2. Operation of the Preferred Embodiment

According to the preferred embodiment, a biometric mobile unit comprises a small handheld application having at least a finger recognition feature. The method of utilizing the biometric unit comprises the following steps: the fingerprint authentication hardware that is installed in the mobile takes the impression of a fingerprint; the biometric unit contacts the web server and transmits the print to the fingerprint authentication hardware comprised on the main server. The print will be compared to the prints stored at the central repository on the main computer until a match properly identifies the client or patient. The information, advanced directives and medical history of the client and/or patient is then displayed on the desktop or the mobile at the provider's station to be utilized in the medical decisions made and the care given; however, the information will not be displayed until the provider identifies himself or herself through a desktop user log-in.

Figure 5:
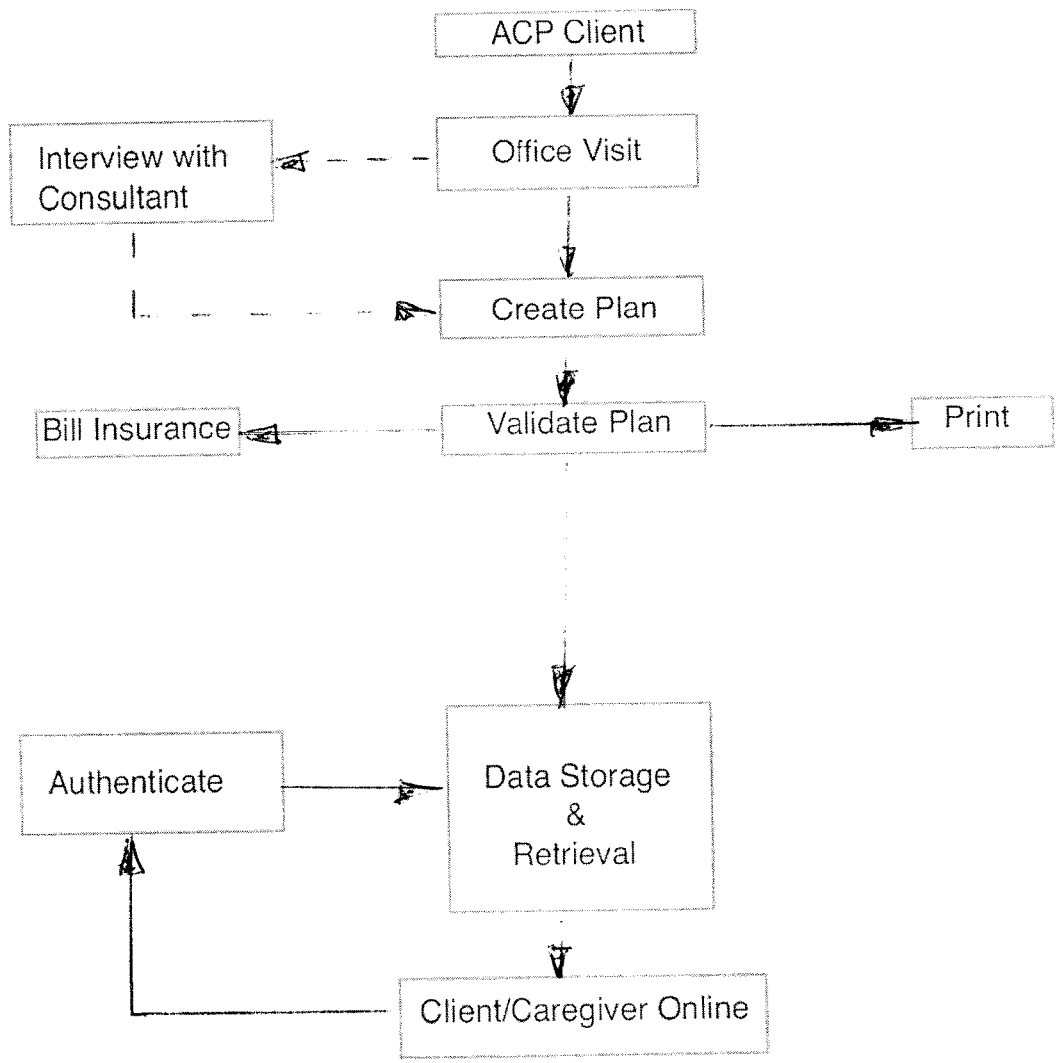
FIG. 5 is a flow diagram showing the system for producing and using an advance care plan in accordance with the present invention.

In operation, as best shown in conjunction with FIG. 5 the present invention provides for a method of collecting, maintaining and transmitting early intervention of life choices, healthcare wishes, financial choices and any or all other aspects of a client's wants which could have meaning in the event of a medical dilemma. The information and documents collected will be combined in an Advance Directive Declarations Packet. The preferred method of collecting client's declarations used in this invention includes hosting seminars for participating clients over the age of 18. These seminars educate clients about their choices and counsel clients through the completion of their respective packet. The completion of the packet, photo ID, fingerprinting of clients and notarization of any legal documents must be completed at the seminar or at a nearby satellite office. On-site notaries and attorneys will legalize documents.

One step of the preferred embodiment requires use of a software program specifically designed around an Advance Directive Declaration Packet for easy implementation, easy instruction and easy education. In accordance with the preferred embodiment, a battery operated, hand held computer is used at seminars with an Advance Directive Declarations Packet and an all-encompassing software program. A wireless Internet™ connection allows for full download of material. The secure computer and its attachments are specifically designed to have the following capabilities: web linking, card servicing, card swiping, card scanning, advertising, optical scanning, photo intaking, printing, battery operated computer packet downloading, fingerprinting, accounting, computer chip downloading, digital downloading of photos, inputting of data, printing of plastic cards, magnetizing to activate cards, holding and storing all data for persons who fill out packets, downloading such data to the main frame for housing, connecting data to a web link, and any and all other inclusive programming in connection with or specific to the use of this invention. The computer used at the time the packet is completed is capable of onsite downloading of all documents to a laptop that sends the information to the mainframe at two or more locations for housing and web link accessibility. The laptop also sends all downloads to machines which activate plastic cards for scanning purposes. A separate classified or declassified web link is provided for government agencies and employees to use for homeland security and military purposes.

Providers accessing Advance Directive Declaration Packets have at their location a receptor computer with web link accessibility to the mainframe, a printer, a computer chip reader, a card scanner, links to upload or download, a fingerprint scanner, a fingerprint reader for cross identification verification, and a keyboard. A highly secure system downloads any or all areas of a packet. The entire packet is immediately issued on a screen when the card is scanned and the provider may highlight and print the appropriate sections for review. Each login is specific to the design. A card is scanned for immediate access to the web link page or an identification number is entered. Clients have a different means of login and access to their information than providers.

The web link provides for specific allowances for advertisements, links to other private and state hospitals, links on recent research, specialties, providers, career information, educational seminars, and any and all other information hospitals would like to share with one another and the public. The web link provides access to all public state health departments, pharmaceuticals, special foundations, state and local court systems, donor registries, etc. Links and advertising is permitted only upon request, special discretion and shared input.

The foregoing descriptions of specific the embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and its various embodiments with various modifications as are suited to the particular use contemplated. It is intended that the scope of the invention be defined by the Claims appended hereto and their equivalents. Therefore, the scope of the invention is to be limited only by the following claims.

Having thus described the invention, what is claimed as new and desired and to be secured by Letters Patent is as follows:

1. A method for creating and using advance health plans and directives of clients, the method comprising:
    creating documented future client specific instructions as part of an interactive explanation and discussion between a qualified professional and the client, the client's family member or the client's surrogate;
    validating the instructions;
    storing the validated instructions in a retrievable electronic format at a computer server and through a communication network;
    obtaining authentication criteria data of the client;
    storing the authentication criteria data in the retrievable electronic format at the computer server and through the communication network;
    associating the validated instructions with the authentication criteria data;
    providing the validated instruction in a Health Insurance Portability and Accountability Act (HIPAA) compliant retrievable electronic format from the computer server and through the communication network to an authenticated requester; and
    billing a third party for the interactive explanation and discussion with the qualified professional, wherein the billing the third party comprises:
        providing a billing code required by the third party; and
        maintaining an audit trail for verification by the third party upon request, the audit trail comprising verification of:
            voluntary completion of the instructions;
            time spent during face-to-face consultation;
            documentation indicating explanation of the instructions; and
            documentation of those present during the face-to-face consultation.

2. The method of claim 1, wherein the documented future client specific instructions are selected from a group comprising: a healthcare power of attorney document; a Do Not Resuscitate order document or Do Not Resuscitate Comfort Care order document; an organ or tissue donation document; a disclosure document; an emergency contact list; any medical form; probate document; advanced directives information relating to a person's own wishes for care; medical history; end of life planning; wills or will substitutes; medical team planning; family planning; funeral planning; estate planning; and an advance care plan for use by hospitals, long term care facilities, nursing homes, rehabilitation centers, substance abuse treatment facilities, insurance companies, donor registries, and all other parties having an interest in a user's health care or end of life care.

3. The method of claim 2, wherein the instructions are created from a previously prepared form of a standardized format capable of being uniquely modified for the client.

4. The method of claim 1, wherein the authentication criteria data is selected from a group comprising: sensing of minutia points; pulse rates; bone structures; DNA; iris scans; facial images; finger prints; card scans; passwords; and user identification.

5. An Advanced Care Planning and life planning data management system comprising a server device including a hardware processor and at least one computer storage medium, the at least one computer storage medium storing a database and database instructions, wherein the database instructions are executable by the hardware processor to:

register a user with the server device by receiving user data including a first biometric identifier of the user through a web interface;

store the user data and the first biometric identifier of the user in the database;

receive health care or life planning information pertaining to the user and store the health care or life planning information in the user data;

assign the first biometric identifier to the user data, the server device and the database being configured to operate remote from the user or any user;

receive, from an individual exigency event requestor, a request including a second biometric identifier of the requestor;

search the database with the server device to identify the first biometric identifier assigned to the health care or life planning information as a match to the second biometric identifier;

transmit at least part of the user data associated with the first biometric identifier to the individual exigency event requestor in response to the request;

update a status of the user in the user data of the database to indicate that the user is in an exigent circumstance and to share such health care or life planning information to a care team or care facility;

receive login information from a life planning computing device at the care team or care facility associated with the exigency event;

conduct a search of the user data in the database to identify patient life planning, advance care planning records indicating that the user is in end of life term, emergency medical event or in transit to the medical care facility during end of life duration; and transmit web page data to a computing device of the care team or care facility during the exigent event indicating of end of life transition, medical event at a caregiver residence, hospice, home care, or medical care facility to generate and display a life planning and care plans having a total number of medical and life decisions from the user and a list identifying, for each identified care plan record: name of the user that is in end of life transition, an estimated time that the user has spent in care planning time, and a notes field identifying current medical status of the user.

6. The Advanced Care Planning and life planning data management system of claim 5, wherein the server device further comprises a web server, and wherein transmitting at least part of the user data is performed by sending data defining a web page.

7. The Advanced Care Planning and life planning data management system of claim 5, wherein the computing device of the care team or care facility is communicatively coupled to a biometric reader and configured to communicate with the server device across the data communication network, wherein the computing device of the care team or care facility reads the second biometric identifier from the requestor and sends the request including the second biometric identifier to the server device.

8. The Advanced Care Planning and life planning data management system of claim 7, wherein the computing device of the care team or care facility is a mobile computing device used by a caregiver, a police officer, an emergency responder, or a military unit.

9. The Advanced Care Planning and life planning data management system of claim 5, further comprising a patient computing device configured to communicate with the server device across the data communication network, wherein the instructions are further executable by the hardware processor to:

receive a request from the patient computing device requesting at least part of the user data;

send to the patient computing device the at least part of the user data;

receive updated user data from the patient computing device; and store the updated user data in place of the user data.

10. The Advanced Care Planning and life planning data management system of claim 5, wherein receiving health care or life planning information pertaining to the user comprises receiving health care information from the computing system of the care team or care facility.

11. The Advanced Care Planning and life planning data management system of claim 5, wherein the user data includes at least some of the following: physician notes, electronic medical records, immunization records, surgical history, medication records, medical treatment records, identification of medical allergies, obstetric history, habit history, family medical history, mental health history, employment history, travel history, family history, common activities, advance directive, living will, and power of attorney for health care.

12. The Advanced Care Planning and life planning data management system of claim 5, wherein the instructions executable to receive from the care team or care facility the request including the second biometric identifier are further executable to:

receive a scanned fingerprint of a registered user from a fingerprint scanner to generate the second biometric identifier at the emergency vehicle computing system; and send the request including the second biometric identifier from the emergency vehicle computing system to the server device.

13. A system for creating, storing and using advance health plans and advanced directives of clients, the system comprising:

a computer server comprising a hardware processor for processing documented future client specific instructions created and validated as part of an interactive explanation and discussion between a qualified professional and a client, the client's family member or the client's surrogate, wherein upon the creation and validation of the documented future client specific instructions, a request for payment for the interactive explanation and discussion between the qualified professional and the client is transmitted to a third party, wherein the request for payment comprises:

providing a billing code required by the third party; and maintaining an audit trail for verification by the third party upon request, the audit trail comprising verification of:

voluntary completion of the instructions;

time spent during face-to-face consultation;

documentation indicating explanation of the instructions; and documentation of those present during the consultation; and an electronic database for storage of the validated instructions in a retrievable electronic format at the computer server and through a communication network;

wherein upon matching of authentication criteria data of a requester with authentication criteria data of the client stored in a computer-readable medium encoded at the computer server, retrieving the validated instructions in a Health Insurance Portability and Accountability Act (HIPAA) compliant electronic format from the computer server through the communication network for use by the requester.

14. The system of claim 13, wherein the documented future client specific instructions are selected from the group comprising: a healthcare power of attorney document; a Do Not Resuscitate order document or Do Not Resuscitate Comfort Care order document; an organ or tissue donation document; a disclosure document; an emergency contact list; any medical form; probate document; advanced directives information relating to the person's own wishes for care; medical history; end of life planning; wills or will substitutes; medical team planning; family planning; funeral planning; estate planning; and an advance care plan for use by hospitals, long term care facilities, nursing homes, rehabilitation centers, substance abuse treatment facilities, insurance companies, donor registries, and all other parties having an interest in a user's health care or end of life care.

15. The system of claim 14, wherein the qualified professional is selected from the group comprising: a physician; a qualified health care professional; a third party consultant functioning as an agent of a physician; a third party consultant functioning as an agent of a qualified health care professional.

* * * * *